(12) United States Patent
Roussouly et al.

(10) Patent No.: US 9,918,847 B2
(45) Date of Patent: Mar. 20, 2018

(54) INTERSOMATIC IMPLANT (71) Applicants: ARTHROPLASTIE DIFFUSION, Saint-Maurice-de Gourdans (FR); Pierre Roussouly, Saint Cyr Au Mont d'or (FR); Radwan Hilmi, Bagnols (FR); Clement Silvestre, Francheville (FR); Pierre Vallese, Bourg en Bresse (FR)

(72) Inventors: Pierre Roussouly, Saint Cyr Au Mont d'or (FR); Radwan Hilmi, Bagnols (FR); Clement Silvestre, Francheville (FR); Pierre Vallese, Bourg en Bresse (FR); Jean-Charles Roussouly, Villeurbanne (FR); Christophe Roy, Chatuzange le Goubet (FR)

(73) Assignee: ADSM, St Maurice de Gourdans (FR)

( * ) Notice: Subject to any disclaimer, the term of this patent is extended or adjusted under 35 U.S.C. 154(b) by 788 days.

(21) Appl. No.: 14/351,212

(22) PCT Filed: Oct. 12, 2012

(86) PCT No.: PCT/FR2012/052327
§ 371 (c)(1),
(2) Date: Apr. 11, 2014

(87) PCT Pub. No.: WO2013/054057
PCT Pub. Date: Apr. 18, 2013

(65) Prior Publication Data
US 2014/0303736 A1   Oct. 9, 2014

(30) Foreign Application Priority Data
Oct. 14, 2011 (FR) ...................... 11 59298

(51) Int. Cl.
*A61F 2/44* (2006.01)
*A61F 2/30* (2006.01)

(52) U.S. Cl.
CPC ............ *A61F 2/442* (2013.01); *A61F 2/4465* (2013.01); *A61F 2002/30156* (2013.01);
(Continued)

(58) Field of Classification Search
CPC .......... A61F 2/44; A61F 2/442; A61F 2/4455; A61F 2/4465; A61F 2/447; A61F 2002/30156; A61F 2002/4475
(Continued)

(56) References Cited

U.S. PATENT DOCUMENTS

| 5,514,180 A | 5/1996 | Heggeness et al. |
| 6,379,385 B1 | 4/2002 | Kalas et al. |

(Continued)

FOREIGN PATENT DOCUMENTS

| WO | 2001049219 A1 | 7/2001 |
| WO | 2004024037 A1 | 3/2004 |

(Continued)

OTHER PUBLICATIONS

International Search Report for corresponding International PCT Application No. PCT/FR2012/052327, dated Jan. 18, 2013.

*Primary Examiner* — Eric S Gibson
(74) *Attorney, Agent, or Firm* — Workman Nydegger (57) ABSTRACT

An intersomatic implant to be inserted into the intervertebral space is defined by two adjacent vertebrae, comprising a body having an upper face and a lower face, parallel to each other. The peripheries of the faces are connected by a vertical peripheral wall. Each of the faces has substantially the shape of a triangle with rounded angles, and each face includes three bearing surfaces located at the three rounded angles of the triangle. At least one of the upper and lower (Continued)

faces is provided with guiding means for the insertion of the implant into the intervertebral space. The guiding means comprises a plurality of ridges directed along an arc of circle, the center of which would be located in the anterior region external to the implant.

11 Claims, 4 Drawing Sheets (52) U.S. Cl.
CPC ............... *A61F 2002/30777* (2013.01); *A61F 2002/30779* (2013.01); *A61F 2002/30784* (2013.01); *A61F 2002/30785* (2013.01); *A61F 2002/30828* (2013.01); *A61F 2002/30904* (2013.01); *A61F 2002/4475* (2013.01); *A61F 2310/00017* (2013.01); *A61F 2310/00023* (2013.01); *A61F 2310/00407* (2013.01)

(58) Field of Classification Search
USPC .................................................. 623/17.16
See application file for complete search history.

(56) References Cited

U.S. PATENT DOCUMENTS

| | | | |
|---|---|---|---|
| 6,458,159 B1* | 10/2002 | Thalgott | A61F 2/4455 606/247 |
| 8,864,829 B1* | 10/2014 | Bruffey | A61F 2/442 623/17.11 |
| 2002/0120334 A1* | 8/2002 | Crozet | A61B 17/86 623/17.11 |
| 2003/0023312 A1* | 1/2003 | Thalgott | A61F 2/4455 623/17.16 |
| 2003/0105527 A1* | 6/2003 | Bresina | A61B 17/1637 623/17.16 |
| 2004/0073314 A1* | 4/2004 | White | A61F 2/4455 623/17.15 |
| 2005/0125062 A1* | 6/2005 | Biedermann | A61F 2/442 623/17.11 |
| 2006/0064169 A1 | 3/2006 | Ferree | |
| 2006/0100705 A1* | 5/2006 | Puno | A61F 2/30771 623/17.11 |
| 2006/0167548 A1* | 7/2006 | Jackson | A61F 2/4455 623/17.11 |
| 2006/0235426 A1* | 10/2006 | Lim | A61F 2/4465 606/99 |
| 2007/0233263 A1* | 10/2007 | Melkent | A61F 2/30771 623/17.16 |
| 2008/0058933 A1* | 3/2008 | Garner | A61F 2/4465 623/17.11 |
| 2008/0077247 A1* | 3/2008 | Murillo | A61F 2/30771 623/17.16 |
| 2008/0147191 A1* | 6/2008 | Lopez | A61F 2/442 623/17.16 |
| 2008/0154375 A1* | 6/2008 | Serhan | A61F 2/441 623/17.16 |
| 2008/0161927 A1* | 7/2008 | Savage | A61F 2/4455 623/17.16 |
| 2008/0188940 A1* | 8/2008 | Cohen | A61F 2/4465 623/17.16 |
| 2008/0312743 A1* | 12/2008 | Vila | A61F 2/442 623/17.16 |
| 2009/0164020 A1* | 6/2009 | Janowski | A61F 2/4465 623/17.16 |
| 2010/0042218 A1* | 2/2010 | Nebosky | A61F 2/3094 623/17.12 |
| 2010/0185292 A1* | 7/2010 | Hochschuler | A61F 2/4455 623/17.16 |
| 2011/0004314 A1* | 1/2011 | Baynham | A61F 2/4465 623/17.17 |
| 2011/0009969 A1* | 1/2011 | Puno | A61B 17/1757 623/17.12 |
| 2011/0166656 A1* | 7/2011 | Thalgott | A61F 2/4465 623/17.16 |
| 2011/0190888 A1* | 8/2011 | Bertele | A61F 2/446 623/17.11 |
| 2011/0230970 A1* | 9/2011 | Lynn | A61F 2/442 623/17.16 |
| 2011/0230971 A1* | 9/2011 | Donner | A61B 17/70 623/17.16 |
| 2012/0158143 A1* | 6/2012 | Shapiro | A61F 2/4455 623/17.16 |
| 2012/0185047 A1* | 7/2012 | Wooley | A61F 2/4465 623/17.16 |
| 2012/0215315 A1* | 8/2012 | Hochschuler | A61F 2/4455 623/17.16 |
| 2013/0096685 A1* | 4/2013 | Ciupik | A61F 2/4465 623/17.16 |
| 2014/0303736 A1* | 10/2014 | Roussouly | A61F 2/4465 623/17.16 |
| 2015/0238324 A1* | 8/2015 | Nebosky | A61F 2/447 623/17.16 |
| 2016/0045333 A1* | 2/2016 | Baynham | A61F 2/4465 623/17.16 |

FOREIGN PATENT DOCUMENTS

| | | |
|---|---|---|
| WO | 2005065596 A1 | 7/2005 |
| WO | 2010021612 A1 | 2/2010 |

* cited by examiner

INTERSOMATIC IMPLANT

BACKGROUND

The present invention relates to an intersomatic implant also called intervertebral implant, intended to be inserted into the intervertebral space defined by two adjacent vertebrae of the vertebral column, also called the spine, to stabilize said vertebrae in a normal anatomical position, after ablation of the defective intervertebral disk.

SUMMARY

Such surgery to replace a damaged intervertebral disk with an implant is called intercorporeal arthrodesis: it may be necessary due to various defects observed on an intervertebral disk. For example, the intervertebral disk may have been compressed across its entire surface and the initial height between the two adjacent vertebrae may have been lost. In other cases, the intervertebral disk may have been compressed asymmetrically, in one of the anterior and/or posterior side regions thereof. The patient may have been suffering from scoliosis. As the vertebral column is the seat of fundamental neurological structures, such phenomena cause pain in patients and it is necessary to remove the defective intervertebral disk and replace it with an implant.

In the present application, an "anterior" region of an intervertebral disk or intersomatic implant refers to the portion of the disk or the implant positioned or intended to be positioned opposite a patient's abdomen. In the present application, the term "anterior region" generally refers to the region of the patient located frontward relative to the vertebral column, in other words the patient's abdomen. In the present application, a "posterior" region of an intervertebral disk or intersomatic implant refers to the portion of the disk or the implant positioned or intended to be positioned opposite the patient's back. In the present application, the term "posterior region" generally refers to the region of the patient located rearward relative to the vertebral column, in other words the patient's back.

Static intervertebral implants for arthrodesis, commonly called "cages", are generally rigid fixed-height wedges with or without a posterior slope. Some of these cages can be hollow to receive materials such as the autogenous bone, synthetic phosphocalcites or osteoinductive agents used to perform fusion between the plates of the adjacent vertebrae, also called secondary fusion. Such secondary fusion keeps correcting the distortion produced by the implantation of the intervertebral implant.

Some existing implants may be adapted to the space created during the ablation of the intervertebral disk prior to implantation. However, only their anteroposterior slope can thus be changed: therefore, these implants only act on the anterior height of the intervertebral space to try to correct the lumbar lordosis.

Other surgical techniques advocate the use of two cages of different heights introduced via a posterior or a posterolateral approach to try to resolve the obliquity of the spine, but introducing said cages requires significant bone resections of the facets, the pedicles or the posterior vertebral arch of the vertebrae concerned, which can aggravate the instability of the column. Moreover, the introduction of such cages carries risks of root or dura mater injury.

Existing implants or cages are generally made in the form of roughly curvilinear and/or convex blocks in an attempt to follow the natural concavity of the vertebral plates. Said concavity is actually oval torus-shaped with a slight central bulge: the shape of existing implants does not allow their correct adaptation to the concavity of the vertebral plates nor the stability needed for bone grafting when it is desired.

It is of course possible to model the vertebral plates to the shape of the implant to create some semblance of stability, but said digging is detrimental to the thin layer of the subchondral bone supporting the disk. As a result, the implant sinks into the cancellous bone of the vertebral body and the intraoperative correction decreases or disappears.

Thus, implants or cages called "PLIF", that is to say, implanted via a posterior approach, are delordosant and have a small graft surface without affecting the subchondral bone. Implants or cages called "TLIF", that is to say, implanted via a posterolateral approach, can restore the lordosis, but often at the expense of the subchondral bone and often with a small graft surface. Finally, implants or cages called "ALIF", that is to say, implanted via anterior approach, require a complicated implantation technique (aortocaval axis retraction): the implant is difficult to wedge between two adjacent vertebrae.

Maladjustment and instability of existing implants are negative factors hindering proper bone fusion, which is itself crucial to sustainable intraoperative correction.

Moreover, the static nature of existing implants does not allow micro-movements to be present to speed up and densify the secondary bone graft.

The present invention seeks to overcome the drawbacks mentioned above.

The present invention relates to an intersomatic implant intended to be inserted in the intervertebral space defined by two adjacent vertebrae, comprising a body having at least an upper face intended to be placed opposite the upper vertebra, and a lower face intended to be placed opposite the lower vertebra, separated from one another by the height of the implant and substantially parallel to each other, the peripheries of said upper and lower faces being connected by a substantially vertical peripheral wall, each of said upper and lower faces having substantially the shape of a convex triangle with rounded angles, each face comprising three bearing surfaces designed to be in contact with the plate of the adjacent vertebra, said bearing surfaces being substantially located in the three rounded angles of said triangle, characterized in that at least one of the upper and lower faces is provided with means for guiding the insertion of the implant into the intervertebral space according to a predetermined direction, said guiding means comprising a plurality of ridges arranged on said face, said ridges being directed according to an arc of circle the center of which would be located in the anterior region external to the implant.

The implant according to the invention generally has the shape of a three legged stand or a tripod intended to rest on three different points of the vertebral plate of the adjacent vertebrae, in particular at the concavity of these plates. The presence of the three bearing surfaces provides the implant with excellent stability. The implant according to the invention makes it possible to restore or correct the height, the sagittal inclination and/or the frontal alignment of the intervertebral space.

Moreover, the implant according to the invention does not require any change, for example by way of digging, of the initial anatomical structure of the vertebral plates and thus makes it possible to respect the integrity of the subchondral bone. The implant according to the invention allows for automatic and immediate adaptation and stability, without artifices or compromise on correction in the three planes, namely the frontal plane, the horizontal plane and the sagittal plane. Furthermore, the particular shape of the implant, namely an overall tripod-like shape, is particularly suitable for a safe introduction of the implant via a retroperitoneal approach.

In an embodiment of the invention, each bearing surface of the upper face is connected to the corresponding bearing surface of the lower face by at least one substantially vertical wall forming a supporting pillar. By "substantially vertical" is meant, according to the present application, that the wall may be slightly inclined relative to the vertical. Thus, the supporting pillars may be vertical or slightly inclined relative to the vertical. The supporting pillars may be parallel to each other or slightly convergent or divergent. The presence of such supporting pillars provides immediate stability of the implant in the intervertebral space. The presence of supporting pillars enhances resistance of the implant which, when the latter is implanted, should withstand the stress exerted on it by both the upper vertebra and the lower vertebra. The contact between the bearing surfaces of the implant and the concave portions of the vertebral plates of the two adjacent vertebrae is thus made optimum.

In an embodiment of the invention, said body is solid. Such an embodiment of the implant according to the invention makes it possible to restore the height of the intervertebral space, the parallelism of the plates of the two adjacent vertebrae, the lumbar lordosis or the front alignment, depending on the height of each supporting pillar, this height being determined by the surgeon according to the defect to be corrected.

In another embodiment of the invention, said body is provided with at least one recess passing through said upper to said lower face. For example, said body is provided with three recesses, each recess corresponding to a central core of a supporting pillar. Alternatively or in combination, at least one of the upper and lower faces, and preferably each face, is provided with one or more non-through recessed portions. The presence of such recesses and/or recessed portions makes it possible to fill the implant with filling material, such as bone grafts, intended to fuse with the bone of the adjacent vertebrae in order to fix the implant to the vertebrae by secondary fusion.

In an embodiment of the invention, said triangle is an isosceles triangle the base of which has a length greater than that of the two equal sides. Such an embodiment allows optimal matching and therefore excellent contact between the bearing surfaces of the supporting pillars of the implant according to the invention and the oval torus-shaped concavity of the vertebral plate of each adjacent vertebra. In particular, as it will be apparent from the following description, the base of the isosceles triangle is located in the anterior region of the implant according to the invention, and the vertex of the isosceles triangle is located in the posterior region of the implant according the invention.

For example, the recesses corresponding to the central cores of the two supporting pillars located at the two similar-sized angles of the isosceles triangle are connected together by a defect of material, said two recesses and the defect of material together forming a continuous kidney-shaped recess. Such a continuous kidney-shape recess perfectly matches the shape of the concavity of the vertebral plates of the adjacent vertebrae. Secondary fusion is thus optimized.

Furthermore, in such a case, preferably, the outer edges of the two supporting pillars located at the two similar-sized angles of the isosceles triangle have a height slightly lower than that of the centers of these supporting pillars. The kidney-like shape of the continuous recess and the reduced height of the outer edges of the supporting pillars promote the introduction of the implant via a limited approach to the intervertebral disk. In comparison, bulkier conventional intersomatic implants require complete resection of the annulus of the disk (fibrous periphery) and therefore it becomes necessary to push completely backward the iliac muscle running along the side face of the lumbar spine. This can have a deleterious effect on the nerve roots passing nearby.

In the implant according to the invention, at least one of the upper and lower faces is provided with means for guiding the insertion of the implant into the intervertebral space along a predetermined direction, in particular along the anterolateral retroperitoneal direction. Such guiding means facilitate the introduction of the implant into the intervertebral space, particularly its insertion between the two vertebral plates of the adjacent vertebrae, such an insertion being made generally in a forcible manner. Thus, said guiding means comprise a plurality of ridges arranged on said face, said ridges being directed along an arc of circle the center of which would be located in the anterior region external to the implant. In particular, the ridges are substantially parallel to each other. Thus, in the implanted position of the implant according to the invention, the center of the arc of circle on which said ridges are aligned is located in the region of the patient's abdomen. Such an embodiment is particularly advantageous for insertion of the implant according to the invention via an anterolateral retroperitoneal approach. Preferably, said guiding means, in particular the arcuate ridges, are present on the upper face and on the lower face of the implant. Thus, once the implant is inserted between the two vertebral plates, the presence of the guiding means, and particularly the arcuate ridges, makes it possible to prevent the implant from moving relative to these two plates and hold it firmly fixed in the position desired by the surgeon, regardless of the approach used to insert the implant between the two vertebrae. Furthermore, the direction of implantation, in particular the anterolateral retroperitoneal implantation, in alignment with the guiding means, namely the arcuate ridges, leads to a concave forward routing of the implant when inserted, thus preventing it from moving towards the back of the vertebral body where it might damage the nerve structures.

In an embodiment of the invention, all supporting pillars are of the same height. Such an embodiment allows simple and immediate reconstitution of the parallelism of the vertebral plates of the adjacent vertebrae.

Alternatively, at least one of the three supporting pillars differs in height from the other two supporting pillars. In yet another embodiment, each supporting pillar has a different height. Such embodiments make it possible to restore the lumbar lordosis or the frontal alignment, as explained in more details below.

BRIEF DESCRIPTION OF THE DRAWINGS

The present invention will become clearer from the following description and the accompanying drawings in which.

DETAILED DESCRIPTION OF VARIOUS EMBODIMENTS

Figure 1:
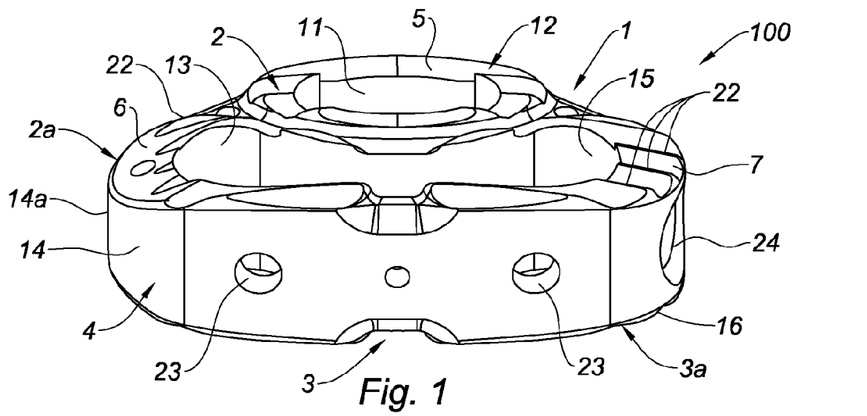
FIG. 1 is a perspective view of an implant according to the invention.

With reference to FIG. 1, an intersomatic or intervertebral implant 100 is shown in perspective according to the invention. As will appear from the description below, particularly with reference to FIGS. 8-10, the implant 100 is intended to be inserted into the intervertebral space defined by two adjacent vertebrae, these vertebrae can be two lumbar vertebrae or the lumbar vertebra L5 and the sacral plate, or two cervical vertebrae.

The implant 100 includes a body 1 having an upper face 2, intended to be placed opposite the upper vertebra (see FIG. 10) when the implant is implanted, and a lower face 3 intended to be placed opposite the lower vertebra (see FIG. 10) when the implant is implanted, the upper face and the lower face being separated from each other by the height H (see FIG. 4) of the implant 100. The material forming the body 1 can be any biocompatible material. For example, the material forming the body 1 of the implant 100 is a material allowing a slight, preferably resilient, deformation of the shape of the implant 100: such an embodiment allows, when the implant 100 contains bone grafts as described below, the potentization of graft during the movements of the spine, to accelerate and improve the quality of the fusion. Preferably, this material is selected from titanium, stainless steel, polymers such as polyetheretherketone, polyetherketoneketone and the admixtures thereof. For example, stainless steel may be coated with titanium.

Figure 4:
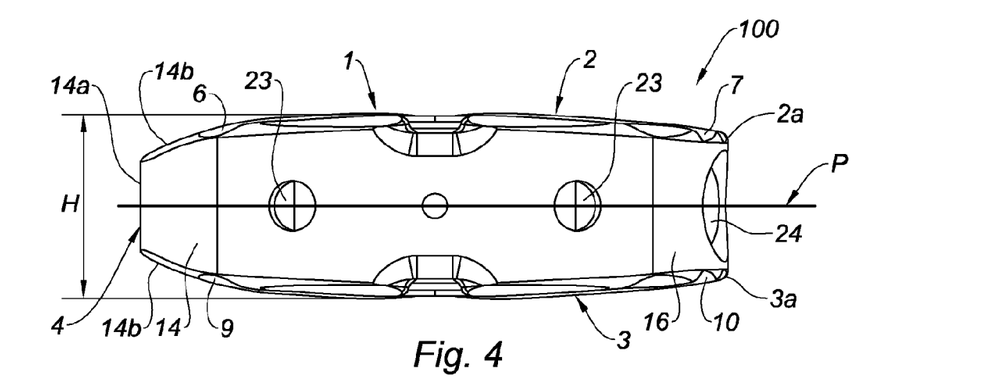
FIG. 4 is a front view of the implant in FIG. 1.
Figure 5:
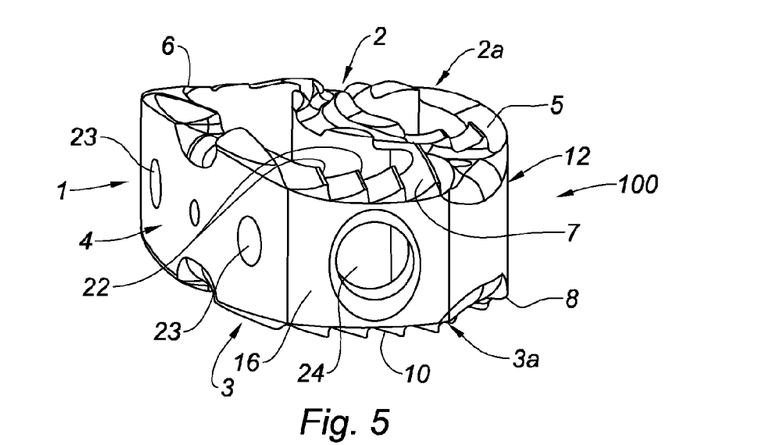
FIG. 5 is a side perspective view of the implant of FIG. 1.

As is apparent from FIG. 4, the upper 2 and lower 3 faces are substantially parallel to each other, that is to say, contained in planes substantially parallel to each other. The upper face 2 has a periphery 2a and the lower face 3 has a periphery 3a. Referring to FIGS. 1, 4 and 5, the peripheries 2a and 3a of the upper 2 and lower 3 faces are connected to each other by a peripheral wall 4, substantially vertical in the example shown. By "substantially vertical" is meant within the scope of the present application that the peripheral wall may be vertical or substantially inclined relative to the vertical, said wall connecting the respective peripheries of the upper and lower faces of the implant over the entire height of the implant. As the implant 100 is intended to replace a defective intervertebral disk, it has a height, designated by H in FIG. 4, substantially equal to the height of an intervertebral disk in its natural undamaged state.

Figure 2:
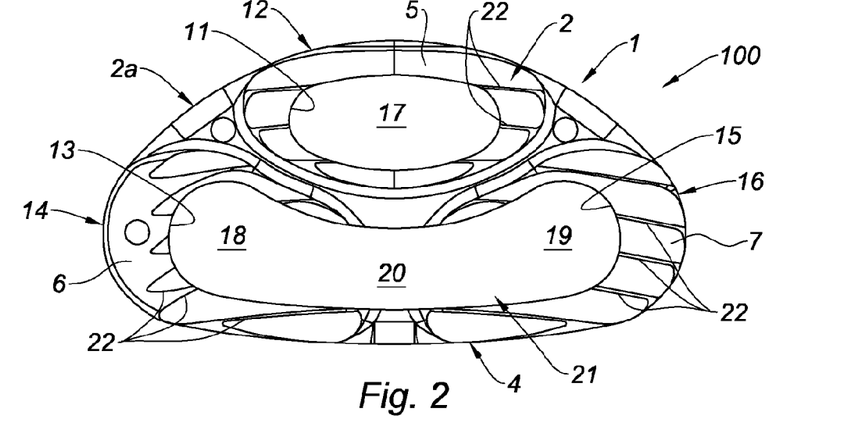
FIG. 2 is a top view of the implant in FIG. 1.
Figure 3:
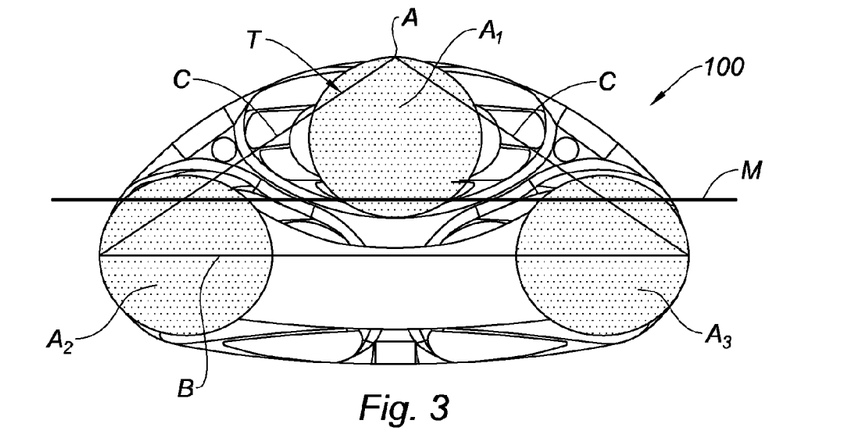
FIG. 3 is a diagram showing the supporting pillars on the implant of FIG. 2.

As is apparent from FIGS. 1 to 3, each face (2; 3) of the implant 100 has substantially the shape of a convex triangle the angles of which would be rounded; in the example shown, the implant 100 is symmetrical with respect to a horizontal plane P passing through half the height H, as shown in FIG. 4.

The triangle defining the convex shape of each face may be of any type, equilateral or isosceles. Preferably, this triangle is isosceles. Preferably, the isosceles triangle has a base of length greater than that of the two equal sides. The isosceles triangle may thus be described as flattened.

The diagram in FIG. 3 helps to visualize such a triangle, which is shown and designated by the letter T. The triangle T, defining the shape of the upper face 2 of the implant 100, is an isosceles triangle having a main vertex A, a base B and two equal sides C, that is to say, of the same length. As shown in FIG. 3, the length of the base B is greater than that of each of the sides C, thus giving the triangle T, and the upper face 2, a flattened appearance. The lower face 3 is identical to the upper face 2 by symmetry relative to the plane P (see FIG. 4).

Figure 7:
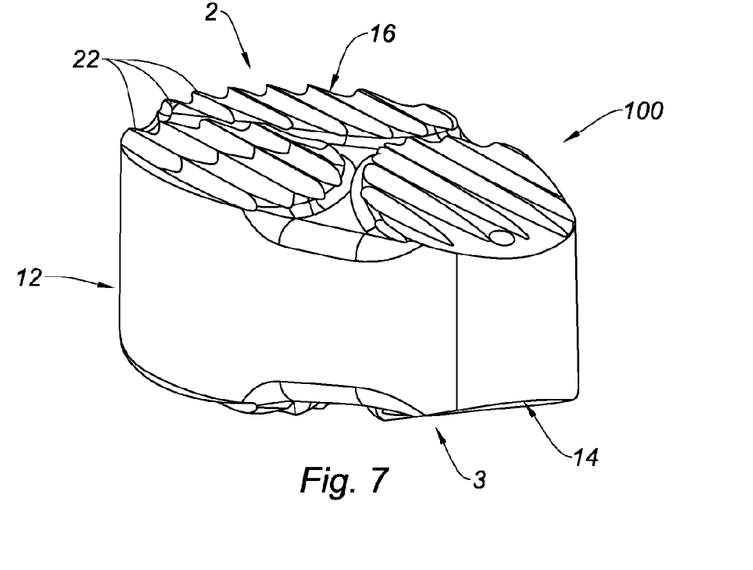
FIG. 7 is a perspective view of the implant of FIG. 6.

In FIG. 3, the rounded angles of the triangle T were diagrammed by the circles A1, A2 and A3: these circles A1-A3 correspond to the bearing surfaces 5, 6 and 7 present on the upper face 2 of the implant 100 as shown in FIG. 2. To said three bearing surfaces correspond on the lower face 3 respectively three bearing surfaces 8, 9 and 10 (see FIGS. 4 and 5), symmetrical with respect to plane P (see FIG. 4): the bearing surfaces (5-10) are intended to be in contact with the plate of the adjacent vertebra when the implant 100 is implanted (see FIG. 10), the bearing surfaces 5-7 of the upper face 2 being intended to be in contact with the plate of the upper vertebra, and the bearing surfaces 8-10 of the lower face being intended to be in contact with the plate of the lower vertebra. As shown in FIGS. 1 and 7, the bearing surfaces (5, 6, 7, 8, 9, 10) of both upper and lower faces (2, 3) of the implant 100 have a slight convexity adapted to the natural concavity of the vertebral plates of the adjacent vertebrae.

For example, each bearing surface may be convex-shaped, for example along a portion of a sphere having a radius ranging from 4 mm to 29 mm, preferably equal to the radius of the concavity of the vertebral plate concerned. For example, the surface of a bearing surface may range between 16 mm$^2$ and 175 mm$^2$.

As will be apparent later in the description, the presence of the three bearing surfaces on the faces of the implant 100 intended to be in contact with the two adjacent vertebrae allows to provide automatic and immediate adaptation and stability, without artifices or compromise on correction in all three planes, namely the frontal plane, the horizontal plane and the sagittal plane.

In particular, in FIG. 3 the median plane M of the spine is shown, when the implant 100 is implanted between two vertebrae. As appears from said Figure, the three bearing surfaces of the implant, represented by the circles A1-A3, are positioned in such a way that their forces are distributed optimally on both sides of the plane M to obtain systematic stability of the implant, irrespective of the state of the vertebral plate surface: the risk that the implant will slide with respect to the vertebral plates of the adjacent vertebrae becomes thus limited.

In the example shown in FIGS. 1-5, each bearing surface (5, 6, 7) of the upper face 2 is connected to the corresponding bearing surface (8, 9, 10) of the lower face 3 by at least one vertical wall forming a supporting pillar: thus, the bearing surface 5 of the upper face 2 corresponding to the vertex A of the triangle T is connected to the corresponding bearing surface 8 (see FIG. 5) of the lower face 3 by a substantially vertical wall 11 forming a supporting pillar 12. The bearing surfaces 6 and 7 of the upper face 2 and corresponding to the other two angles of the triangle T are connected to the corresponding bearing surfaces 9 and 10 (see FIG. 4) of the lower face 3 respectively by substantially vertical walls 13 and 15 forming respectively the supporting pillars 14 and 16.

The presence of supporting pillars reinforces the resistance of the implant 100 which, when implanted, must withstand the stress exerted on it by both the upper vertebra and the lower vertebra. The contact between the bearing surfaces of the implant and the bearing surfaces of the vertebral plates of the two adjacent vertebrae is thus made optimum. In particular, as apparent in FIG. 9, such an embodiment where the triangle defining the shape of the faces of the implant is isosceles provides optimal matching and therefore excellent contact between the bearing surfaces of the supporting pillars of the implant according to the invention and the oval torus-shaped concavity of the vertebral plate of each adjacent vertebra.

In the example shown in FIGS. 1-5, the implant 100 is provided with recesses passing through the upper face 2 to the lower face 3. In the example shown, these recesses are three in number and generally correspond to a central core of each supporting pillar. Thus, the supporting pillar 12 is crossed by a central recess 17. The supporting pillars 14 and 16 are each crossed by central recesses 18 and 19, said two recesses being connected together by a defect of material 20 to form a continuous kidney-shaped recess 21 (see FIG. 2).

Alternatively or in combination, in an embodiment not shown, at least one of the upper and lower faces, and preferably each face, is provided with recessed, non-through portions.

The presence of such recesses and/or recessed portions allows the implant 100 to be filled with filling material, such as bone grafts, intended to fuse with the bone of the adjacent vertebrae in order to fix the implant to the vertebrae.

Figure 6:
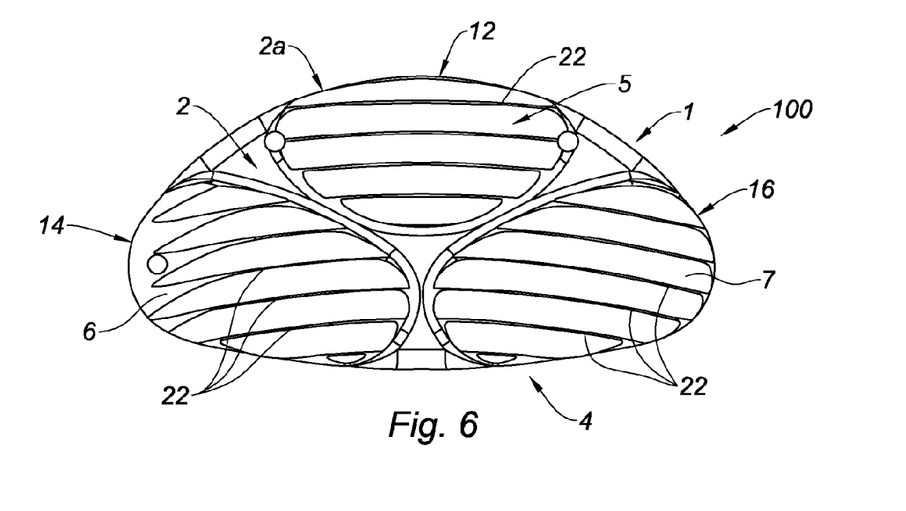
FIG. 6 is a top view of another embodiment of an implant according to the invention.

In the embodiment of the implant 100 according to the invention shown in FIGS. 6 and 7, for which the reference numerals denoting the same elements as in FIGS. 1-5 have been preserved, the body 1 is solid and therefore devoid of recesses. Such an implant can restore the required height between two vertebrae. Furthermore, when secondary fusion is not necessary, such an embodiment allows simple and immediate reconstitution of the parallelism of the plates, the lumbar lordosis or the front alignment, depending on the respective heights of the supporting pillars, as explained below.

In the examples shown in FIGS. 1-10, the three supporting pillars 12, 14 and 16 are substantially of the same height. Such an embodiment allows simple and immediate reconstitution of the parallelism of the vertebral plates of the adjacent vertebrae. Also in the examples shown in FIGS. 1-10, the outer edges of the two supporting pillars (14, 16) located at the two similar-sized angles of the isosceles triangle have a height slightly lower than that of the centers of these supporting pillars: thus, as shown in FIG. 4, the upper and lower faces 14b of the supporting pillar 14 are inclined.

In other embodiments not shown, at least one supporting pillar has a height different from the height of the other two supporting pillars. In the present description, a posterior pillar, intended to be placed at the posterior region of the vertebral plates of the adjacent vertebrae, refers to the supporting pillar 12, and an anterior pillar, to be placed at the anterior region of the vertebral plates of the adjacent vertebrae refers to the supporting pillars 14 and 16. Thus, the posterior pillar 12 is located in the posterior region of the implant 100, and the anterior pillars (14, 16) are located in the anterior region of the implant 100. For example, when the posterior pillar 12 has a height smaller than the height of the two anterior pillars 14 and 16, simple and immediate reconstitution of the lumbar lordosis becomes possible. Another example is the one where one of the anterior pillars (14, 16) has a height greater than that of the other anterior pillar (16, 14) with, for example, the posterior pillar being of a height with a value ranging between the values of the two anterior pillars: in such a case, the front alignment can be reconstituted for example to correct scoliosis or offset a cuneiform vertebra.

In other embodiments not shown, each supporting pillar has a different height. Such embodiments may be useful in the context of specific deformations.

In the embodiments of the implant 100 shown in FIGS. 1 to 10, the upper face 2 is provided with a plurality of ridges 22: as seen on the diagram in FIG. 3, the ridges 22 are substantially parallel to each other and are curved along an arc of circle the center of which would be located in the anterior region external to the implant, that is to say, the region of the abdomen when the implant 100 is implanted in a patient, and the radius of which would range between 5 mm and 500 mm. As will be apparent from the description of FIGS. 8-10, the curvilinear direction of said ridges corresponds to the direction of the insertion of the implant 100 when it is implanted between two adjacent vertebrae via an anterolateral retroperitoneal oblique approach: the ridges thus form means for guiding the implant 100 during its forcible insertion between the two vertebrae. The ridges 22, by causing a concave forward routing of the implant 100 during its insertion via an anterolateral retroperitoneal oblique approach (see FIG. 8), protect the nearby nerve structures by preventing the implant from moving towards the back of the vertebral column. Furthermore, as shown in FIG. 5, the lower face 3 of the implant 100 is also provided with ridges 22 having the same direction as the ridges 22 of the upper face 2.

As shown in FIG. 1, the implant 100 may further comprise side ports 23: such ports may be useful for example to receive a tool in the case where ablation of the implant becomes necessary.

In the embodiment shown in FIGS. 1-5, the implant 100 is further provided with a side port 24 located at its supporting pillar 16: this side port 24 is intended to receive the tool for installing the implant 100 during its forcible insertion between the two vertebrae. In an embodiment not shown, it is also possible to fix in the side port 24 an additive osteosynthetic plate with a screw for the purpose of fixing the implant and the two adjacent vertebrae by screwing in each of the vertebrae. Furthermore, as shown in FIGS. 1 and 4, the outer vertical wall 14a of the supporting pillar 14 has a height slightly lower than the height H of the implant 100 and the upper and lower faces 14b of the supporting pillar 14 are inclined. Indeed, as the implant 100 is intended to be forcibly inserted between two vertebrae by the supporting pillar 14, the inclined faces 14b of the supporting pillar 14 are atraumatic and facilitate the introduction of the implant 100 in the intervertebral space.

Figure 8:
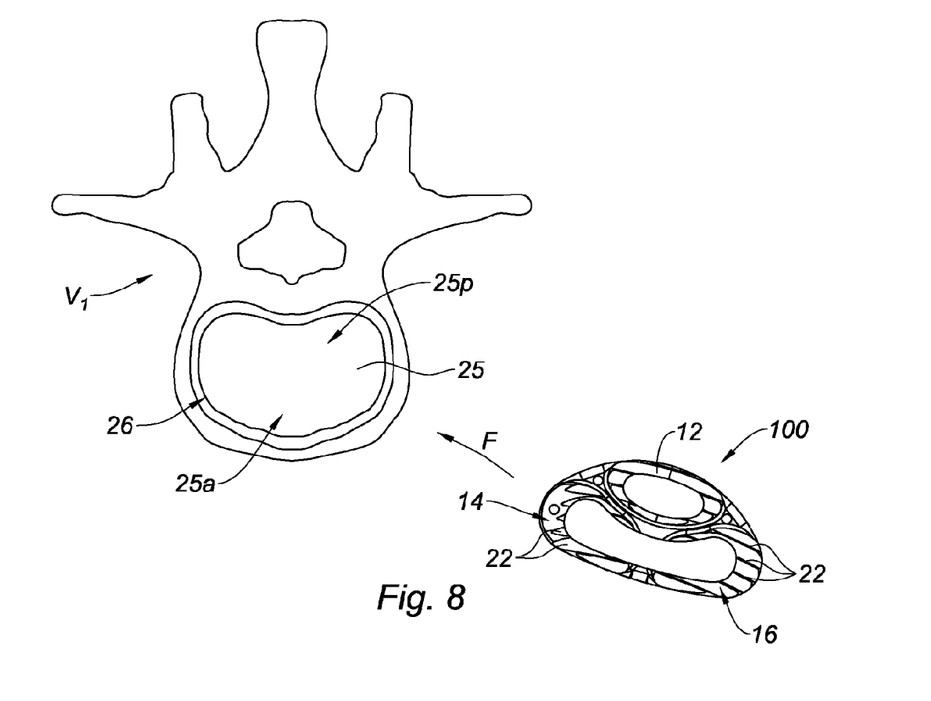
FIG. 8 is a schematic view of the surgical approach used in the insertion of the implant according to the invention.
Figure 9:
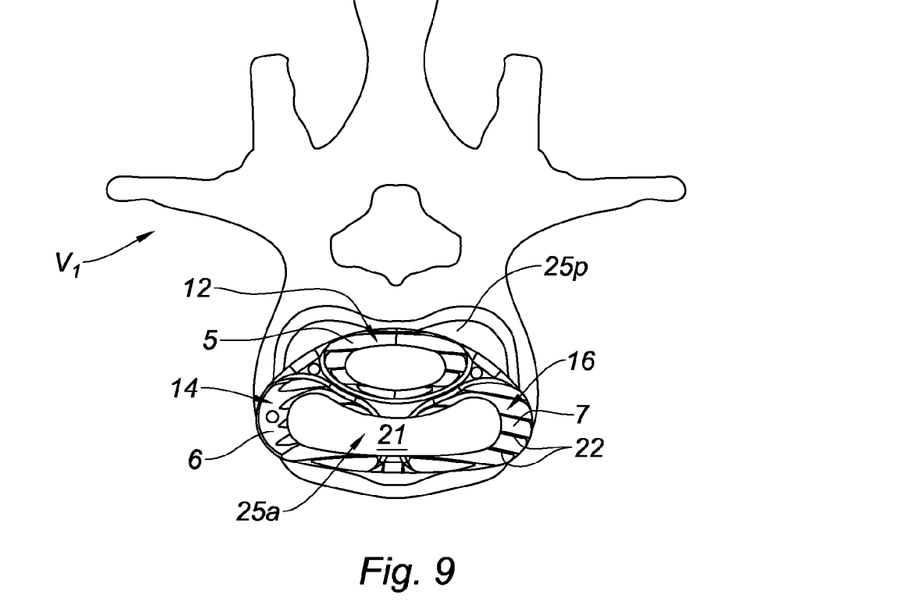
FIG. 9 is a schematic top view of the implant according to the invention once inserted between two vertebrae.
Figure 10:
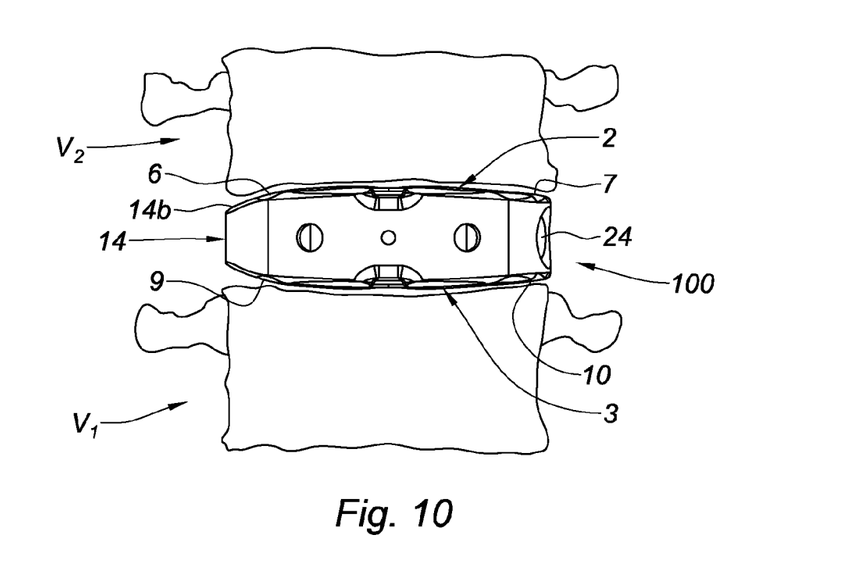
FIG. 10 is a side view of the implant according to the invention, once inserted between two vertebrae.

Referring to FIGS. 8-10, the following is a description of the surgical technique used in inserting the implant 100 according to the invention between two vertebrae, the intervertebral disk of which is defective and needs to be replaced.

FIG. 8 shows a top view of vertebra V1 with its vertebral plate 25. The anterior region 25a of the vertebral plate is positioned opposite the patient's abdomen (not shown) while the posterior region 25p of the vertebral plate 25 is positioned toward the patient's back. Said both regions 25a and 25p have a concavity disposed along an oval torus 26 shown schematically in FIG. 8. The implant 100 according to the invention is intended to be inserted between the lower vertebrae V1, and the upper vertebra V2 (see FIG. 10), in the direction indicated by the arrow F in FIG. 8, in other words, via an anterolateral retroperitoneal oblique approach. As shown in FIG. 8, the ridges 22 are substantially parallel to the direction of the insertion F and they will constitute guiding means for the insertion of the implant 100 between the two vertebrae V1 and V2, so that the posterior pillar 12 of the implant 100 are positioned at the concavity of the posterior region 25p of the vertebral plate 25 and that both anterior pillars 14 and 16 of the implant 100 are positioned at the concavity of the region 25a of the vertebral plate 25 of the vertebra V1 (same for V2), as shown in FIG. 9.

Referring to FIGS. 8-10, the implant 100 is inserted by first approaching the supporting pillar 14 of the intervertebral space: as seen above, the fact that the supporting pillar 14 has inclined upper and lower faces 14b facilitates the insertion of the implant 100 between the two vertebrae V1 and V2. The implant 100 is forcibly inserted between the two vertebrae by means of a tool (not shown) one end of which is received in the side port 24 and by gently rotating the implant 100 in the direction of the ridges 22 in order to position the implant 100 as explained above and as shown in FIG. 9.

Referring to FIG. 10, the implant 100 is now implanted in the intervertebral space defined by two adjacent vertebrae V1 and V2. Thanks to the ridges 22 in particular, the implant 100 is firmly maintained in the position desired by the surgeon: the arcuate ridges 22 allow such maintaining in position, regardless of the approach used to install the implant 100. As apparent from the above Figure, the ridges 22 are parallel to an arc of circle the center of which is located in the anterior region of the patient beyond the implant 100, that is to say, in the region of the abdomen (not shown) of the patient, in the median plane of the patient's body.

Such an implant according to the invention makes it possible to restore the height of the intervertebral space, the parallelism of the plates of two adjacent vertebrae, a lumbar lordosis or the front alignment, depending on the height of each supporting pillar, the height being determined by the surgeon according to the defect to be corrected.

When the implant 100 comprises bone grafts, the latter will fuse with the vertebral plates of the vertebrae V1 and V2 in order to perpetuate the correction of the deformation by implanting the implant according to the invention.

The invention claimed is:

1. An intersomatic implant intended to be inserted into a intervertebral space defined by two adjacent vertebrae, comprising:
    a body having at least one upper face intended to be placed opposite an upper vertebra, and a lower face intended to be placed opposite a lower vertebra, separated from each other by a height of the implant and, the body having an anterior side and a posterior side corresponding to an anterior posterior plane of the intervertebral space,
    peripheries of said upper and lower faces being connected together by a substantially vertical peripheral wall,
    each of said upper and lower faces having substantially the shape of a convex triangle with three rounded angles, such that two of the three rounded angles are provided on the anterior side of the body,
    each face comprising three bearing surfaces intended to be in contact with a plate of the adjacent vertebra, said bearing surfaces being substantially located at the three rounded angles of said triangle;
    wherein at least one of the upper and lower faces is provided with guiding means for the insertion of the implant into the intervertebral space along a predetermined direction, said guiding means comprising a plurality of ridges arranged on said at least one of the upper and lower faces, each of said plurality of ridges being directed along an arc of a circle, the center of which would be located in an anterior region external to the implant, such that the guiding means lead to a forward concave routing of the intersomatic implant when inserted via anterolateral retroperitoneal implantation.

2. The implant according to claim 1, wherein each bearing surface of the upper face is connected to the corresponding bearing surface of the lower face by at least one substantially vertical wall forming a supporting pillar.

3. The implant according to claim 2, wherein the supporting pillars are of the same height.

4. The implant according to claim 2, wherein at least one of the supporting pillars has a height different from a height of two other supporting pillars.

5. The implant according to claim 2, wherein the supporting pillars are of different heights.

6. The implant according to claim 1, wherein said body is provided with at least one recess passing through said upper face to said lower face.

7. The implant according to claim 2, wherein said body is provided with three recesses, each recess corresponding to a central core of a supporting pillar.

8. The implant according to claim 7, wherein said triangle is an isosceles triangle, a base of which has a length greater than that of two equal sides.

9. The implant according to claim 8, wherein recesses corresponding to central cores of two supporting pillars located at two similar-sized angles of the isosceles triangle are connected together by a defect of material, said recesses and the defect of material together forming a continuous kidney-shaped recess.

10. The implant according to claim 9, wherein outer edges of the two supporting pillars located at the two similar-sized angles of the isosceles triangle have a height slightly smaller than that of centers of the two supporting pillars.

11. The implant according to claim 1, wherein said ridges are present on the upper face and on the lower face of the implant.

* * * * *